(12) United States Patent
Pohl et al.

(10) Patent No.: US 9,733,170 B2
(45) Date of Patent: Aug. 15, 2017

(54) SORPTION OF WATER FROM A SAMPLE USING A POLYMERIC DRYING AGENT

(71) Applicant: DIONEX CORPORATION, Sunnyvale, CA (US)

(72) Inventors: Christopher A. Pohl, Union City, CA (US); Kannan Srinivasan, Tracy, CA (US); S M Rahmat Ullah, Fremont, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 15/259,422

(22) Filed: Sep. 8, 2016

(65) Prior Publication Data

US 2016/0377516 A1 Dec. 29, 2016

Related U.S. Application Data

(62) Division of application No. 13/415,373, filed on Mar. 8, 2012, now Pat. No. 9,459,184.

(51) Int. Cl.
| | |
|---|---|
| *G01N 1/34* | (2006.01) |
| *G01N 1/40* | (2006.01) |
| *B01D 11/04* | (2006.01) |
| *G01N 1/10* | (2006.01) |
| *C08F 220/34* | (2006.01) |
| *C08F 228/02* | (2006.01) |
| *C08F 220/06* | (2006.01) |

(Continued)

(52) U.S. Cl.
CPC ......... *G01N 1/405* (2013.01); *B01D 11/0492* (2013.01); *B01J 20/261* (2013.01); *C08F 220/06* (2013.01); *C08F 220/34* (2013.01); *C08F 228/02* (2013.01); *G01N 1/10* (2013.01); *G01N 1/34* (2013.01); *G01N 1/4055* (2013.01); *B01D 11/04* (2013.01); *C08F 222/1006* (2013.01); *G01N 2001/4061* (2013.01)

(58) Field of Classification Search
CPC ...... B01D 11/04; B01D 11/0492; G01N 1/10; G01N 1/34; G01N 1/405; G01N 1/4055; G01N 2001/4061
See application file for complete search history.

(56) References Cited

U.S. PATENT DOCUMENTS

| | | |
|---|---|---|
| 3,062,739 A | 11/1962 | Crits |
| 4,293,427 A | 10/1981 | Lucas et al. |
| 4,874,520 A | 10/1989 | Lee |

(Continued)

FOREIGN PATENT DOCUMENTS

| | | |
|---|---|---|
| EP | 2226192 A1 | 9/2010 |
| WO | 9831083 | 7/1998 |

(Continued)

OTHER PUBLICATIONS

Anabolicminds Archive, "Beginners Guide to Soxhlet Extractions," Anabolicminds Archive, Apr. 1, 2003.

(Continued)

*Primary Examiner* — Katherine Zalasky
(74) *Attorney, Agent, or Firm* — Timothy J. Ohara (57) ABSTRACT

A method of extracting an analyte from a sample is described where the sample includes water. The sample and polymeric drying agent are added to a container. The polymeric drying agent includes a cationic monomer, an anionic monomer, and a crosslinker. The polymeric drying agent is configured to sorb water from the sample.

15 Claims, 6 Drawing Sheets

(51) Int. Cl.
    B01J 20/26     (2006.01)
    C08F 222/10    (2006.01)

(56) References Cited

U.S. PATENT DOCUMENTS

| | | | |
|---|---|---|---|
| 5,002,670 | A | 3/1991 | Pratt |
| 5,368,850 | A | 11/1994 | Cauwet et al. |
| 5,562,963 | A | 10/1996 | Davis |
| 5,616,407 | A | 4/1997 | Fritz et al. |
| 5,647,976 | A | 7/1997 | Rothe et al. |
| 5,785,856 | A | 7/1998 | Gleave et al. |
| 5,843,311 | A | 12/1998 | Richter et al. |
| 6,087,339 | A | 7/2000 | Hindsgaul |
| 6,187,887 | B1 | 2/2001 | Albrecht et al. |
| 6,391,204 | B1 | 5/2002 | Russo, Jr. |
| 6,492,183 | B1 | 12/2002 | Perman et al. |
| 6,616,893 | B1 | 9/2003 | Pham |
| 6,984,705 | B2 | 1/2006 | Chang et al. |
| 7,399,403 | B2 | 7/2008 | Garcia, III et al. |
| 7,582,482 | B2 | 9/2009 | Dasgupta et al. |
| 2002/0004535 | A1 | 1/2002 | Kotsuka et al. |
| 2003/0047513 | A1 | 3/2003 | Burton et al. |
| 2003/0178370 | A1 | 9/2003 | Fisk et al. |
| 2005/0274662 | A1 | 12/2005 | Xie |
| 2006/0000778 | A1 | 1/2006 | Childs et al. |
| 2007/0111194 | A1 | 5/2007 | Pellaux et al. |
| 2009/0221079 | A1 | 9/2009 | Srinivasan et al. |
| 2011/0237468 | A1 | 9/2011 | Reichenbach-Klinke et al. |
| 2012/0028368 | A1 | 2/2012 | Srinivasan et al. |
| 2012/0029154 | A1 | 2/2012 | Deetz et al. |

FOREIGN PATENT DOCUMENTS

| | | |
|---|---|---|
| WO | 0104201 | 1/2001 |
| WO | 2005058453 A1 | 6/2005 |
| WO | 2005102503 A1 | 11/2005 |
| WO | 2006095093 | 9/2006 |
| WO | 2012015379 | 2/2012 |

OTHER PUBLICATIONS

AOAC Official Method 922.06, AOAC Official Methods of Analysis, 1996 AOAC International, 32.1.14.

AOAC Official method 932.06, AOAC Official Methods of Analysis, 2006 AOAC International, 33.5.08.

AOAC Official Method 989.05, AOAC Official Method of Analysis, 2006 AOAC International, 33.2.26.

Aveldano et al., "Quantitative release of fatty acids from lipids by a simple hydrolysis procedure," J of Lipid Research, 24, 1101-1105, 1983.

Burford, M.D., et al., "Evaluation of drying agents for off-line supercritical fluid extraction," J. of Chromatography A, 657, 413-427, 1993.

Camel, V., "Recent extraction techniques for solid matrices—supercritical fluid extraction, pressurized fluid extraction and microwave-assisted extraction: their potential and pitfalls," Analyst, 126, 1182-1193 2001.

Castro et al., "Soxhlet extraction of solid materials: an outdated technique with a promising innovative future," Analytica Chimca Acta, 369, 1-10, 1998.

Dionex, "Accelerated Solvent Extraction (ASE®) Sample Preparation Techniques for Food and Animal Feed Samples," Dionex Technical Note 209, 2006.

Dionex, "Methods Optimization in Accelerated Solvent Extraction (ASE®)," Dionex Technical Note 208, 2004.

English, A.E. et al., "Equilibrium swelling properties of polyampholytichydrogels," J. Chem. Phys., 104(21), 8713-8720, 1996.

Hang & Yin, "Research on new technology of polyvinyl alcohol," Sci. & Tech. in Chem. Industry, 17(4), 52-56, 2009.

Hennion, "Solid-phase extraction: method development, sorbents, and coupling with liquid chromatography," J of chromatography A, 856, 3-54, 1999.

Joshi et al., "Analysis of drugs of abuse from whole human blood," BIOforum Europe, retrieved from internet site: http://www.millipore.com/bibliography.nsf/a73664f9f981af8c852569b9005b4eee/7f7197f9a63c40cf8525722c0052dd8c/$FILE/BioForumEurope1006.pdf, 2006.

Mandal, V., et al., "Microwave assisted extraction—an innovative and promising extraction tool for medicinal plant research," Pharmacognosy Reviews, 1(1), 7-18, 2007.

Neyret, S., et al., "The properties of polyampholyte microgel particles prepared by microemulsion polymerization," Polymer, 38(25), 6129-6134, 1997.

Obana, H., et al., "Determination of acephate and methamidophos in foods using super-absorbent polymer," Analytical Communications, 34, 253-256, 1997.

Obana, H., et al., "Multiresidue analysis of pesticides in vegetables and fruits using a high capacity absorbent polymer of water," Analyst, 124, 1159-1165, 1999.

Ridgeway et al., "Sample preparation techniques for the determination of trace residues and contaminants in foods," J. of Chromatography A, 1153, 36-53, 2007.

Sigui et al., "Manual of Fine Chemicals and Intermediates," Chemical Industry Press, p. 637, Sep. 30, 2004.

Skoog et al., Analytical Chemistry, An Introduction, Chapter 13, Saunders College Publishing, 6th ed., pp. 227-236, 1994.

US EPA Method 3545A, Pressurized Fluid Extraction (PFE), 10 pages, Jan. 1998.

US EPA, National Exposure Research Laboratory, Method 314.0, Determination of perchlorate in drinking water using ion chromatography, 49 pages, Nov. 1999.

Xiumin, "Comprehensive Chemical Experiment," Beijing Normal University Publishing Group, pp. 88-89, Jun. 30, 2007.

Zhou et al., "Development of a hydrothermal deposition process for applying zirconia coatings on BWR materials for IGSCC mitigation," Corrosion Science, 49, 830-843, 2006.

SORPTION OF WATER FROM A SAMPLE USING A POLYMERIC DRYING AGENT

CROSS-REFERENCE TO RELATED APPLICATION

This application is a Divisional under 35 U.S.C. §120 and claims the priority benefit of co-pending U.S. Non-provisional application Ser. No. 13/415,373, filed on Mar. 8, 2012, entitled "SORPTION OF WATER FROM A SAMPLE USING A POLYMERIC DRYING AGENT," the entire disclosure of which is incorporated by reference

BACKGROUND

More effective monitoring of trace organic compounds such as pesticides and environmental toxins has become increasingly important. Examples of sample matrices that are monitored include soil, oil, water, fruits, vegetables, foams, and carpets.

Quite often, an untreated sample cannot be tested directly in an analytical instrument. Typically, a sample extraction process is performed first, which is a process for separating the compound of interest (i.e. analyte) from the sample matrix. A sample extraction can include treating the sample with an organic solvent to preferentially dissolve the analyte and separate it from other components of the sample. The organic solvent containing the dissolved analyte can then be tested with an analytical instrument. In other instances, the organic solvent may be removed or at least partially removed to concentrate the analyte before performing the analytical test. Examples of analytical instruments suitable for analyzing an extracted sample are gas chromatography and liquid chromatography with suitable detectors such as a mass spectrometer, ultraviolet-visible spectrometer, fluorimeter, flame ionization detector, electrochemical detector, and the like A particular type of solvent extraction is accelerated solvent extraction (ASE). This technique is performed using an organic solvent at an elevated temperature and pressure. The elevated pressure increases the solvent boiling point thereby allowing a liquid extraction to be conducted at higher solvent temperatures. In general, a higher temperature will speed up analyte dissolution and the extraction process.

Many trace organic compounds of interest have the property of being volatile or semi-volatile. A challenge in monitoring such compounds is that many types of sample matrices contain water or residual moisture. Drying the sample in an oven is not a viable option because the volatile and semi-volatile compounds can also be removed from the sample. The presence of water can interfere with the extraction process efficiency. For example, the presence of an aqueous phase with dissolved analyte will decrease the extraction efficiency into the organic solvent. If solvent evaporation is needed, the analyte can preferentially concentrate into the aqueous phase and make the analysis more difficult.

The presence of water can also interfere with the analytical method. Analytical techniques such as gas chromatography (GC) and gas chromatography/mass spectrometry (GC/MS) can be sensitive to moisture depending on the type of stationary phase materials.

One approach for removing residual water from an organic phase involves the addition of an insoluble inorganic salt that sorbs water. This technique is also referred to as "salting out" in the literature. When the analyte tends to partition between the aqueous phase and the organic phase, recovery in the organic phase decreases. To counter this effect, an inorganic salt that has a high affinity for the aqueous phase is added. The salt sorbs water and forms a hydrate, which causes the analyte to shift from the aqueous phase to the organic phase. Thus, the addition of salt causes the analyte to preferentially dissolve into the organic phase. Salts such as sodium sulfate, calcium chloride, magnesium sulfate, and calcium sulfate may be used for the purpose of moisture removal. The organic solvent phase is removed after the salt exposure by filtration or by decanting. The process for removing the salt by filtration can be difficult because it tends to clump together when water is present. The inorganic salt is typically added in increments so as to prevent an excess amount from being added. Filters can be easily clogged or take a large amount of time to filter the organic solvent making the process difficult to automate. Applicants believe that there is a need to develop a drying agent that can efficiently and effectively sorb water and be easily separated from the organic solvent such that the process can be automated.

Instead of salts, polymeric drying agents can also be used to remove water from a sample. An example of such a polymeric drying agent is the sodium salt of polyacrylic acid. Although this polymeric drying agent removes water by absorbing it into the polymer matrix, the water absorbing capacity decreases as the ionic strength increases. Since most sample ionic strengths are not known a priori, it would be difficult to use this polymeric drying agent particularly with unknown samples that may have a high ionic strength. Another limitation of polyacrylic acid is that it absorbs water poorly under higher temperature conditions.

Applicants believe that there is a need to develop a drying agent that can efficiently and effectively sorb water at both elevated temperature and pressure so that it can be used with accelerated solvent extraction and other extraction techniques such as supercritical fluid extraction, microwave extraction, Soxhlet extraction and the like. In addition, applicants believe that there is a need for the drying agent to efficiently and effectively sorb water for a sample containing a wide range of salt concentrations. This would allow the drying agent to be used with a wide range of sample types.

SUMMARY

A method of extracting an analyte from a sample is described. The sample and a polymeric drying agent are added to a container. The polymeric drying agent includes a cationic monomer, an anionic monomer, and a crosslinker. Next, a solvent can be dispensed to the container. The analyte can dissolve from the sample into the solvent. The polymeric drying agent can sorb water within the container. The solvent can be removed from the container and analyzed for the analyte using a suitable analytical technique. In an embodiment, substantially all of the water is sorbed within the container by the polymeric drying agent.

A method of drying a sample where the sample includes water is described. The sample and a polymeric drying agent are added to a container. The polymeric drying agent includes a cationic monomer, an anionic monomer, and a crosslinker. The polymeric drying agent can sorb water from the sample to the polymeric drying agent. In an embodiment, substantially all of the water is sorbed from the sample by the polymeric drying agent.

A method of drying a solvent where the solvent includes water is described. A polymeric drying agent is added to the solvent. The polymeric drying agent includes a cationic monomer, an anionic monomer, and a crosslinker. The polymeric drying agent can sorb water from the solvent. In an embodiment, substantially all of the water is sorbed from the solvent by the polymeric drying agent.

An apparatus for extracting a compound from a sample includes a solvent pump, a container, and a heater. The solvent pump can be configured to transfer the solvent to the container. The container can include a polymeric drying agent and be configured to receive the sample. The polymeric drying agent includes a cationic monomer, an anionic monomer, and a crosslinker. The heater can be configured to heat up the solvent.

A polymeric drying agent for binding water during a liquid extraction of a compound from a sample is described. The polymeric drying agent includes a cationic monomer, an anionic monomer, and a crosslinker. The cationic monomer can be a weak base and the anionic monomer can be a weak acid. The weak base has a tertiary amine and the weak acid has a carboxylate.

A method of making a polymeric drying agent is described. A reaction mixture can be prepared that includes dimethylaminoethylacrylate, acrylate, polyethylene glycol diacrylate, [2,2'-azobis (2-amidinopropane) dihydrochloride], and water in a container. Next, the container is heated to form the polymeric drying agent.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements). A detailed understanding of the features and advantages of the present invention will be obtained by reference to the following detailed description that sets forth illustrative embodiments, in which the principles of the invention are utilized, and the accompanying drawings of which.

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

Figure 4:
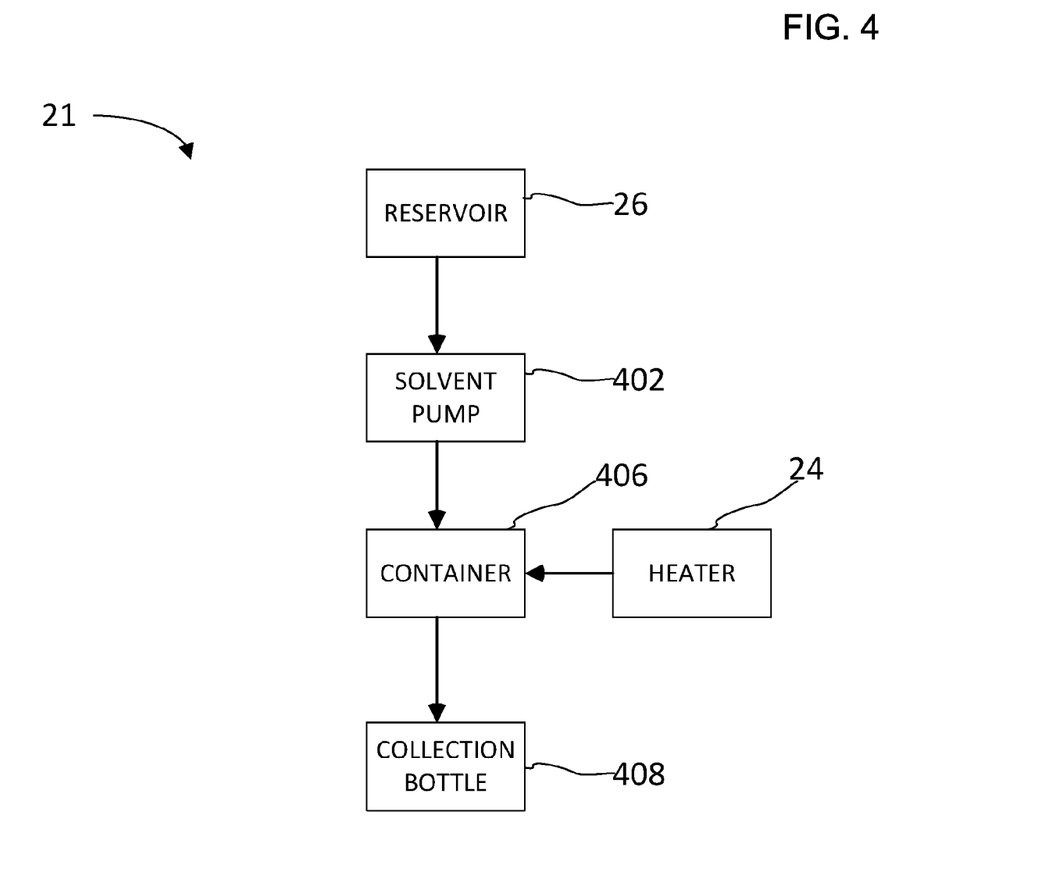
FIG. 4 illustrates a simplified schematic of an accelerated solvent extraction apparatus.

A description of an apparatus suitable for use in accelerated solvent extraction will be described. FIG. 4 illustrates a simplified schematic of an accelerated solvent extraction apparatus 21 that includes a reservoir 26, a solvent pump 402, a heater 24, a sample container 406, and a collection bottle 408. Reservoir 26 is a vessel configured to store a solvent such as, for example, an organic solvent. The organic solvent is a solvent that contains carbon and is selected based on the ability of the solvent to dissolve the analyte. Examples of organic solvents suitable for use in solvent extraction may be hexane, acetone, methylene chloride, petroleum ether, toluene, acetic acid, methane sulfonic acid, and combinations thereof. In an alternative embodiment, an inorganic solvent can be used in combination with an organic solvent such as, for example, phosphoric acid and toluene. Examples of inorganic solvents that may be used include hydrochloric acid, phosphoric acid, and ammonia. For the situation where the extraction solvent itself intrinsically contains water, a post extraction drying step with a polymeric drying agent may be required. Solvent pump 402 is configured to transfer a solvent from reservoir 26 to sample container 406. Sample container 406 is configured to hold a sample that is subjected to the accelerated solvent extraction process. Sample container 406 is also configured to transfer the solvent with dissolved analyte to collection bottle 408. Heater 24 is configured to heat up the solvent. In addition, heater 24 may be proximate to sample container 406 so that it can be heated and/or pressurized to a predetermined level. The sample container 406 can be configured to be a closed container during the heating process causing the pressure within the container to increase.

Figure 5:
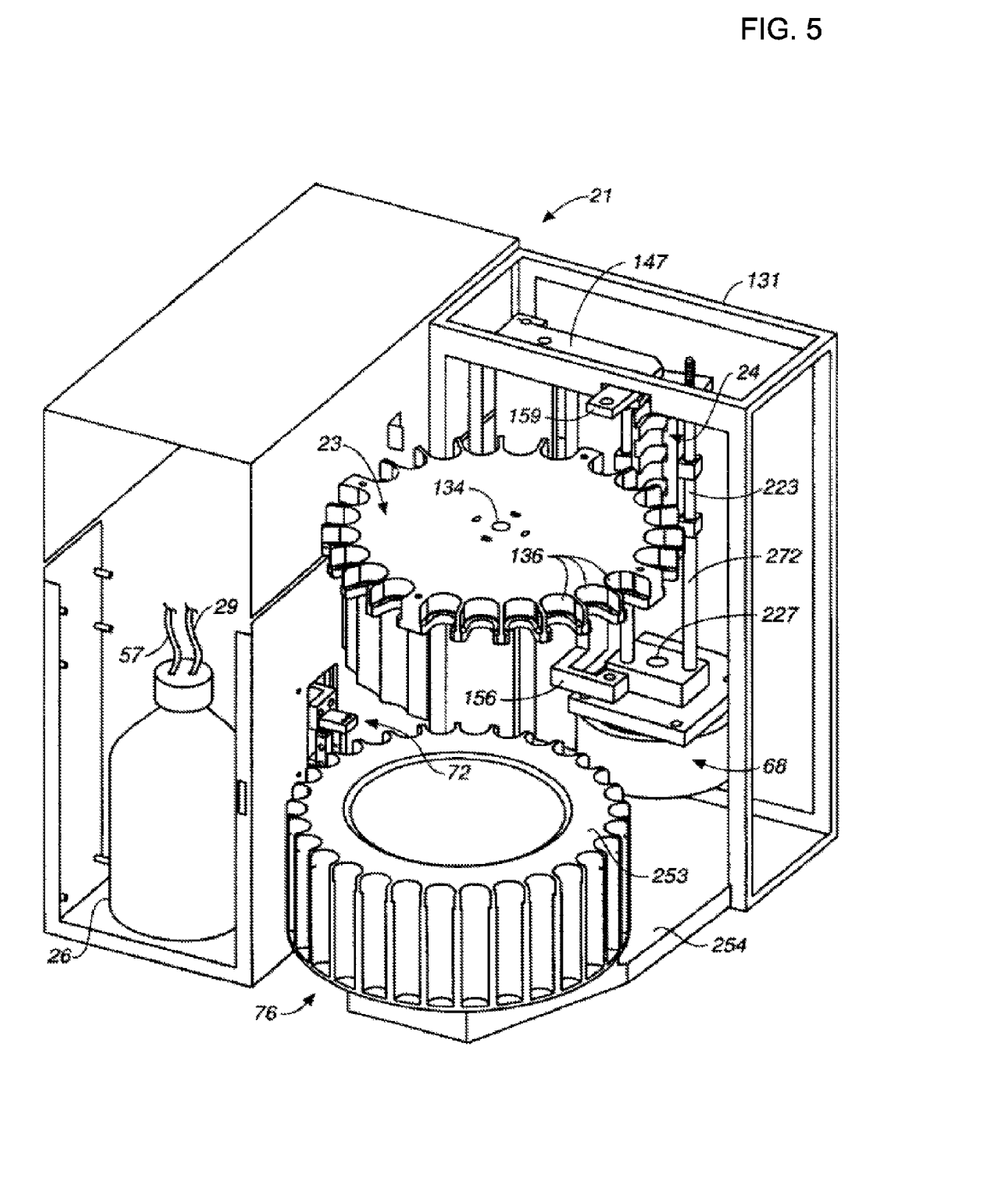
FIG. 5 illustrates a simplified perspective view of an accelerated solvent extraction apparatus.

FIG. 5 illustrates a simplified perspective view of accelerated solvent extraction apparatus 21 that includes a turntable 23 and a collection bottle assembly 253 for allowing an automated solvent extraction process on a plurality of samples. Such an apparatus is commercially available from Thermo Scientific (Dionex Inc., Sunnyvale, Calif., part number 066050, ASE 350). Turntable 23 includes a plurality of support bays 136 configured to hold a plurality of sample containers so that several samples can be extracted in an automated fashion. An opening 134 on turntable 23 is coupled to a motor so that turntable 23 can be rotated. Collection bottle assembly 253 includes a collection rack 76 configured to hold a plurality of collection bottles so that solvent containing analyte can be transferred from a sample container to a corresponding collection bottle. Collection bottle assembly 253 is rotatably mounted to a base structure 254. A needle assembly 72 is configured to transfer solvent from the sample container to the collection bottle. More details regarding accelerated solvent extraction can be found in U.S. Pat. Nos. 5,647,976; 5,785,856; 5,843,311; and US Pre-Grant Publication Number 2012/0028368, which are hereby fully incorporated by reference herein.

Referring back to FIG. 5, apparatus 21 includes solvent reservoir 26 that is fluidically connected to a solvent pump via conduits 27 and 59. An assembly to dispense solvent to the sample container and to transfer solvent to the collection bottle includes the following elements: an upper arm 159, an upper assembly arm member 147, a rod member 223, a needle 272, an upper end 227, and a clamp actuator 68. Apparatus 21 also includes a housing framework 131 and a heater 24.

Figure 6:
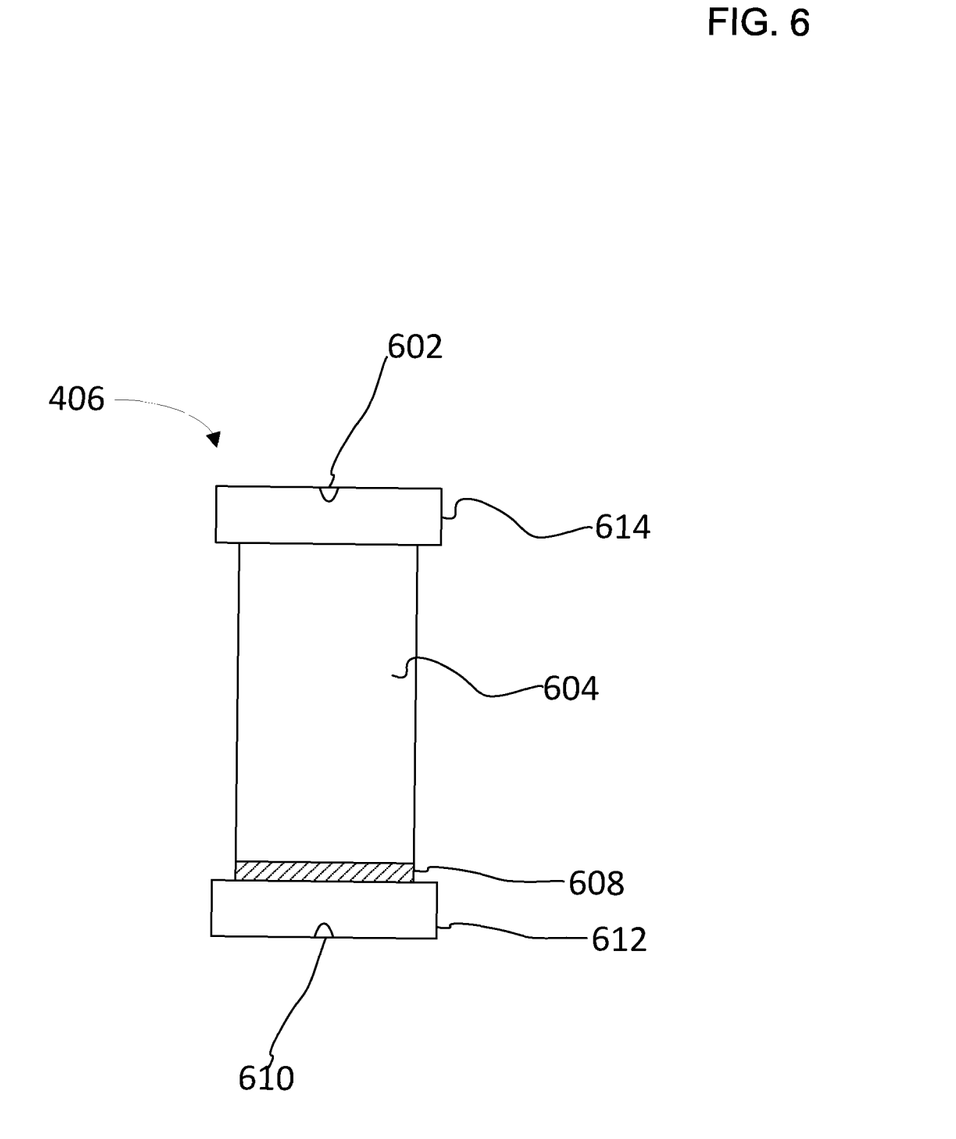
FIG. 6 illustrates a simplified schematic of a container configured to be used with an accelerated solvent extraction apparatus.

FIG. 6 illustrates a simplified schematic of a container 406 configured to be used with an accelerated solvent extraction apparatus. Container 406 can have an approximately hollow cylindrical cavity 604 with a first cap 614 and a second cap 612. Both first cap 614 and second cap 612 are configured to close the open ends of cylindrical cavity 604. The caps 614, 612 can include a threaded arrangement to attach to a corresponding outer portion of the cylinder. First cap 614 includes an inlet 602 configured to receive solvent pumped from reservoir 26. Second cap 612 includes an outlet 610 configured to transfer solvent to the collection bottle. Container 406 also includes a frit 608 that is attached to a bottom portion of the cylinder so that solvent can be filtered during the process of transferring solvent to the collection bottle. Container 406 can be configured to have a volume ranging from about 1 milliliter to about 1000 milliliters.

Now that an accelerated solvent apparatus has been described, the following will describe a method of using the apparatus to extract analyte from a sample. Once second cap 612 is secured to the base of hollow cylindrical cavity 604, a sample can be added to sample container 406. Depending on the sample type, the sample may be ground up or pulverized into a powder first. Next, first cap 614 can be secured to container 406 and then mounted to the accelerated solvent apparatus. A solvent can be dispensed into the container to dissolve the analyte into the solvent. In order to speed up the extraction process, an elevated pressure and temperature can be applied to the container for a period of time. The elevated pressure can be a value that is greater than ambient pressure, and more specifically may range from about 100 pounds per square inch to about 1500 pounds per square inch. The elevated temperature can be a value that is greater than ambient, and more specifically may range from about 40° C. to about 200° C. In an embodiment, the duration of incubating the sample with solvent may range from about 5 minutes to about 60 minutes. After the analyte has dissolved, the solvent containing the dissolved analyte can be removed from the container and transferred to the collection bottle via outlet 610.

For many sample types that typically contain water, this can interfere with the efficiency of the extraction process. For this reason, applicants believe that there is a need to remove water from the sample in a way that is compatible with a solvent extraction and more particularly with an accelerated solvent extraction process. In an embodiment, a polymeric drying agent can be added to the sample to sorb water. For the case of accelerated solvent extraction that can be performed in an automated fashion, applicant believes that the polymeric drying agent should be able to sorb water at elevated temperature, elevated pressure, over a range of salt concentrations, be amendable to filtration without clogging, and have a relatively high capacity to sorb water per polymeric drying agent weight.

Figure 3:
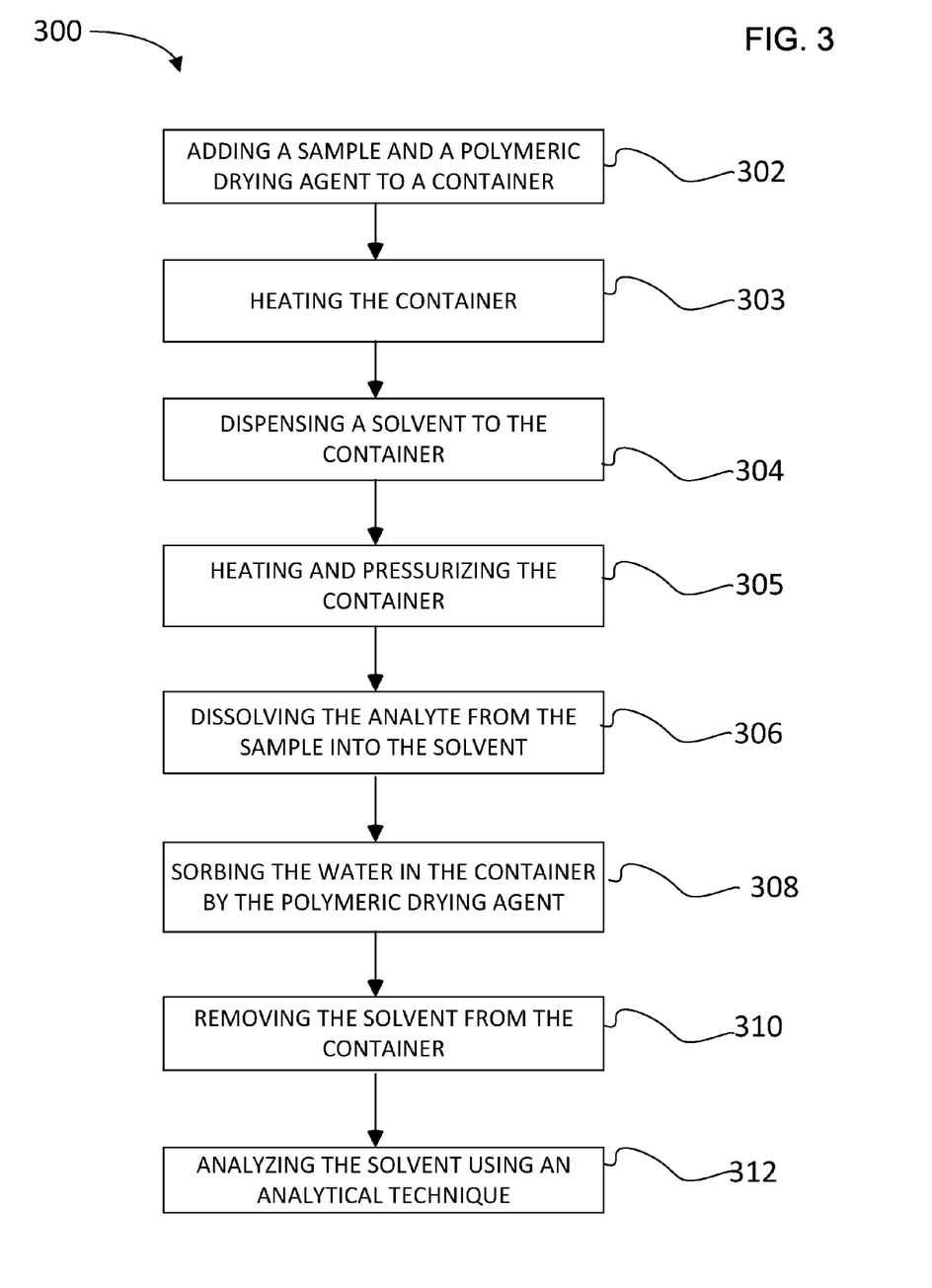
FIG. 3 is a flow chart that illustrates a method of sorbing water from a sample using a polymeric drying agent.

FIG. 3 is a flow chart illustrating a method 300 of sorbing water from a sample using a polymeric drying agent. The sample and the polymeric drying agent can be added to a container, as shown in a step 302. The polymeric drying agent can start to sorb water from the sample upon contact. Before the adding step, the sample and the polymeric drying agent may be ground or mixed together to facilitate the sorption process and/or the extraction process. Optionally, an inert media such as a sand or a diatomaceous earth may be added to the sample and polymeric drying agent together. The inert media can provide more pathways for the solvent to be transported and improve the contact with the polymeric drying agent. In an alternative embodiment, the polymeric drying agent can be added to the container beforehand and/or be integrated into frit 608.

Once the sample and polymeric drying agent has been added to the container, the sample container may be heated, as shown in a step 303. The elevated temperature may be a value that is greater than ambient. More specifically, the elevated temperature may range from about 40° C. to about 200° C.

A solvent such as, for example, an organic solvent can be dispensed into the container, as shown in a step 304. In many cases, there will be insoluble matrix materials that do not dissolve in the solvent. The container can be heated and pressurized, as shown in step 305. In the presence of solvent, the elevated temperature may be a value that is greater than ambient. More specifically, the elevated temperature may range from about 40° C. to about 200° C.

It should be noted that the heating process will cause the pressure to increase to a value greater than ambient when the container is sealed (i.e., inlet 602 and outlet 610 are both closed). The combination of heat and pressure generally causes the solvent to have an elevated temperature and remain in the liquid phase. More specifically, the increased pressure may range from about 100 pounds per square inch to about 1500 pounds per square inch. In an embodiment, the increased pressure is sufficiently high so that the solvent does not boil.

Analyte dissolves from the sample into the solvent, as shown in a step 306. The polymeric drying agent sorbs water in the container, as shown in a step 308. In an embodiment, substantially all of the water is sorbed within the container by the polymeric drying agent.

The sorbing of water by a polymeric drying agent includes a binding of water at the peripheral surface of the polymer particle and/or the binding of water within the crosslinked polymer network. The polymeric drying agent binds water sufficiently strong such that it does not associate with either the analyte or solvent. After water is sorbed by the polymeric drying agent, the solvent and analyte can be removed from the container so that they are substantially free of water to the extent that the extraction efficiency can be relatively high and an analytical technique can be performed without interference. In an embodiment, substantially free of water may describe a situation where a person cannot see the visible presence of water in a container. Typically, water can be visible to a person when there is about 100 microliters of water or more in the container. It should be noted that the extraction of analyte from a sample in container 406 using elevated temperature and pressure may be referred to as an "in-cell" extraction.

In another embodiment, the solvent can be in the form of a supercritical fluid. A supercritical fluid can be any substance at a temperature and pressure above its critical point, where distinct liquid and gas phases do not exist. Examples of supercritical fluids suitable for use with the polymeric drying agents described herein may be carbon dioxide, methane, ethane, propane, ethylene, propylene, methanol, ethanol, water, ammonia, acetone, toluene, and combinations thereof. Modifiers may be added to the supercritical solvent. For example, $CO_2$ can be combined with toluene or methanol. It should be noted that where the supercritical fluid itself contains water that a post-extraction drying step may be required. More details regarding supercritical fluid extraction can found in Camel et al., Analyst, volume 126, (2001) pp. 1182-1193, which is hereby fully incorporated by reference herein.

Referring back to steps 303 and 305, the process of heating can be performed using a resistive heater where current flows through a resistive element to provide a predetermined amount of heat to the container. Alternatively, a microwave power source may be used for one of steps 303 and 305 or for both of the steps. The microwave power can be directed to the container, the sample, the solvent, or a combination thereof. More details regarding microwave assisted extraction can found in Camel et al.

After the sample has incubated, the solvent is removed from the container, as shown in a step 310. In an embodiment, the solvent is removed via outlet 610. In this process, the solvent is filtered through frit 608. Insoluble matrix materials and the polymeric drying agent should remain in the container and not clog the filtering process. In particular, polymeric drying agent should be configured so that it does not clog the filter so that the process can be easily automated. In addition, the filtering process should be relatively fast so that sample throughput can be relatively high. It should be noted that an excess of polymeric drying agent can be added to the container without affecting the filter time. The ability to add an excess of polymeric drying agent provides a convenience to the user in that the polymeric drying agent does not have to be added incrementally so as to prevent clumping of excess drying agent in the container. The solvent can be transferred to a collection bottle and stored for the subsequent analysis step.

Under certain circumstances where more stringent drying is required, an amount of polymeric drying agent can be added to the collection bottle. This may be referred to as "off-cell" drying. If necessary, the polymeric drying agent can be removed from the collection bottle by a subsequent filtering process or decanting. Otherwise, the polymeric drying agent can be allowed to settle to a bottom of the bottle and an aliquot may be removed from an upper portion of the solvent. Accordingly, a sample can be extracted using a combination of an in-cell and an off-cell drying process where higher performance drying is required.

For circumstances where an in-cell process (i.e. accelerated solvent extraction) is not needed, an "off-cell" only configuration can be used where the solvent, polymeric drying agent, and sample are combined to extract the analyte without applying heat or pressure. The solvent can dissolve the analyte from the sample. The polymeric drying agent can sorb water from the solvent to the polymeric drying agent. After moisture removal, the solvent containing the dissolved analyte can be processed for analysis. In an embodiment, substantially all of the water is sorbed from the solvent by the polymeric drying agent. The solvent with dissolved analyte has substantially all of the water removed when water is not visible in the sample and/or the solvent is sufficiently dry so that an analytical technique can be performed on the sample in an accurate manner.

Once the solvent is removed from the container, it can be analyzed using an analytical technique, as shown in a step 312. Optionally, all or a portion of the solvent can be removed by evaporation or distillation so that the analyte can be concentrated before performing the analytical technique. After method 300, the sample container is substantially free of water. In turn, the solvent and/or analyte is also substantially free of water so that an analytical technique can be performed in an accurate manner.

It should be noted that in some cases the extraction step can be omitted where the polymeric drying agent removes water from the sample by direct contact. In this case, a solvent is not added. For example residual moisture in a sample can be removed by simply contacting the sample with the polymeric drying. The polymeric drying agent can sorb water from the sample to the polymeric drying agent. After moisture removal, the sample containing analyte can be directly processed for analysis in an analytical instrument. Alternatively, the dried sample containing analyte may then be extracted with a solvent. In an embodiment, substantially all of the water is sorbed from the sample by the polymeric drying agent. A sample has substantially all of the water removed when water is not visible in the sample and/or the sample is sufficiently dry so than an analytical technique can be performed in an accurate manner.

In another embodiment, a Soxhlet extraction can be performed using the polymeric drying agents described herein. The sample can be added to a porous container. The polymeric drying agent can be added to the porous container and/or the distilling pot. The distilling pot contains a hot solvent that creates solvent vapor. The solvent vapor can go through the porous container and then extract the analyte from the sample. In this process, the polymeric drying agent can sorb water directly from the sample and also from the solvent contained in the distilling pot. More details regarding Soxhlet extraction can be found in Castro et al., Analytica Chimica Acta, volume 369 (1998) pp. 1-10, which is hereby fully incorporated by reference herein.

In another embodiment, the polymeric drying agents described herein can be used to dry a solvent that contains neither a sample nor an analyte. A polymeric drying agent can be added to the solvent containing water. The polymeric drying agent can sorb water from the solvent. After removing the polymeric drying agent, the dried solvent can be stored or used for a process.

The following will describe polymeric drying agents suitable for use in method 300. In an embodiment, the polymeric drying agent can be a copolymer that includes a first monomer, a second monomer, and a crosslinker. The first monomer can be in the form of a cationic monomer and the second monomer can be in the form of an anionic monomer. The cationic monomer includes a positive charge. More specifically, the cationic monomer may include one or more of the following functional groups such as primary amines, secondary amines, tertiary amines, and quaternary amines. The anionic monomer includes a negative charge. More specifically, the anionic monomer may include one or more of the following functional groups such as carboxylic acids and sulfonic acids.

Figure 1A:
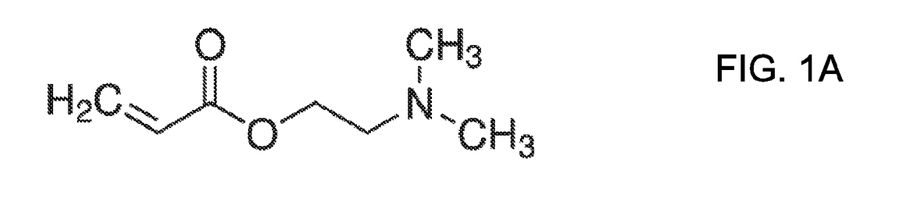
FIG. 1A illustrates a chemical structure of dimethylaminoethylacrylate, which is suitable for use as a cationic monomer that includes a weak base.
Figure 1B:
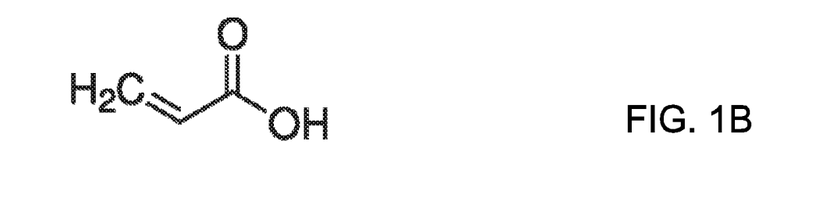
FIG. 1B illustrates a chemical structure of acrylic acid, which is suitable for use as an anionic monomer that includes a weak acid.
Figure 1C:
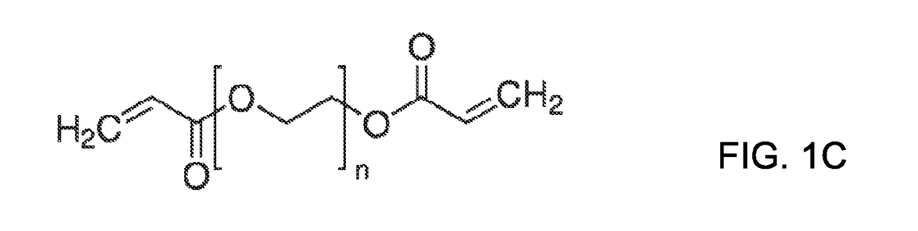
FIG. 1C illustrates a chemical structure of polyethylene glycol diacrylate, which is suitable for use as a crosslinker.

For a first copolymer, the cationic group can be a weak base and the anionic group can be a weak acid. The weak base may be a tertiary amine and the weak acid can be a carboxylic acid. The cationic monomer can include dimethylaminoethylacrylate, the anionic monomer can include acrylic acid, and the crosslinker can include polyethylene glycol diacrylate, which are illustrated in FIGS. 1A to 1C, respectively. In an embodiment, the weak base can have a pKa ranging from about 8 to 10 and the weak acid can have a pKa ranging from 3 to about 5.

In alternative embodiments of the first copolymer, the cationic monomer may be acrylate based such as dimethylaminoethylacrylate, dimethylaminoethylmethacrylate, dimethylaminopropylacrylamide, dimethylaminopropylmethacrylamide or be styrenic based such as dimethylaminobenzylstyrene or diethylaminoethylstyrene or tert-butylaminoethylmethacrylate or combinations thereof. In alternative embodiments of the first copolymer, the anionic monomer can be acrylic acid, methacrylic acid, vinylbenzoic acid, 2-carboxyethyl acrylate, 2-acrylamidoglycolic acid or combinations thereof.

For the first copolymer, a molar ratio of the cationic monomer to the anionic monomer may be about 1:1 so that the salt form of the monomer pair is present (e.g. dimethylammoniumethylacrylate-acrylate salt) along with the cross-linking agent. The copolymer combination simulates a salting out like environment absorbing the moisture while the analyte is preferentially distributed in the organic phase. The copolymer can have a net neutral charge so as to reduce the possibility that the copolymer will sorb a charged analyte molecule.

The first copolymer is configured to sorb water even under high ionic strength conditions. When the first copolymer has a molar ratio of about 1:1 with respect to the cationic monomer and the anionic monomer, the overall net charge is about zero. Thus, anions and cations (i.e. salt) at high ionic strength can associate with water molecules and diffuse into the interior of the first copolymer. Although a molar ratio of 1:1 has been described for providing water sorbing characteristics over a range of ionic strength levels, variation from this ratio can be implemented and still provide a copolymer capable of sorbing water, but at a lower capacity.

In contradistinction, a polymer with a net negative or net positive charge will repel ions from entering the polymer matrix. An example of a net negative polymer is the sodium salt of polyacrylic acid. At relatively low ionic strength, this polymer will allow the neutral water molecules to enter the polymer matrix and repel negatively charged ions. However, at high ionic strength, most of the water molecules are associated with charged ions and cannot penetrate the polymer matrix. Thus, when the charged ions on the exterior of the copolymer reach a certain concentration, there is little water sorbance by the polymer. Overall, the net effect is a decrease in the water uptake of the polymer with a net negative or net positive charge. Accordingly, a net zero charge copolymer having a plurality cationic and anionic groups will sorb water more effectively over a range of salt concentrations.

Figure 2A:
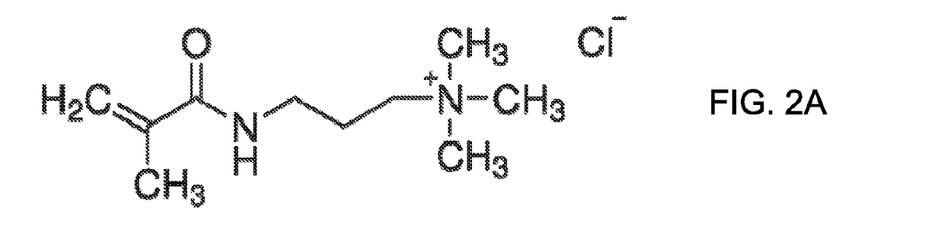
FIG. 2A illustrates a chemical structure of [3-(methylacryloylamino)propyl]trimethylammonium chloride, which is suitable for use as a cationic monomer that includes a strong base.
Figure 2B:
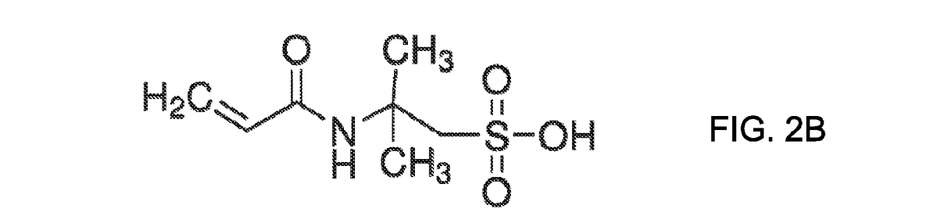
FIG. 2B illustrates a chemical structure of 2-acrylamido-2-methyl-1-propanesulfonic acid, which is suitable for use as an anionic monomer that includes a strong acid.
Figure 2C:
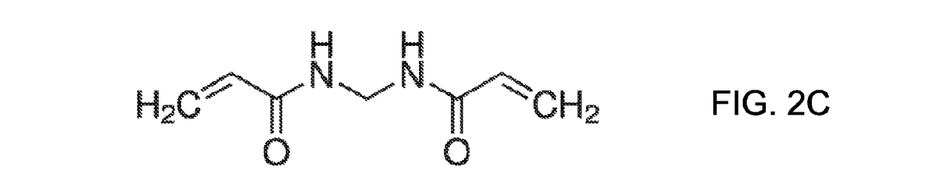
FIG. 2C illustrates a chemical structure of N,N'-methylenebis(acrylamide), which is suitable for use as a crosslinker.

In another embodiment, a second copolymer includes a cationic monomer, an anionic monomer, and a crosslinker where the cationic monomer can include a strong base and the anionic monomer can include a strong acid. The strong base can be a quaternary amine and the strong acid can be a sulfonic acid. The cationic monomer can include [3-(methylacryloylamino)propyl]trimethylammonium chloride, the anionic monomer can include 2-acrylamido-2-methyl-1-propanesulfonic acid, and the crosslinker can include N,N'-methylenebis(acrylamide), which are illustrated in FIGS. 2A to 2C, respectively. In an embodiment, the strong base can have a pKa greater than ten and the strong acid can have a pKa less than three. In a preferred embodiment, the strong acid can have a pKa of about less than or equal to one. For the second copolymer, the molar ratio of the cationic monomer to the anionic monomer can be about 1:1 so that the salt form of the monomer pair is present.

In another embodiment, a third copolymer includes a cationic monomer, an anionic monomer, and a crosslinker where the cationic monomer can be a strong base and the anionic monomer can be a weak acid. In yet another embodiment, a fourth copolymer includes a cationic monomer, an anionic monomer, and a crosslinker where the cationic monomer can be a weak base and the anionic monomer can be a strong acid. For both the third and fourth copolymer, the molar ratio of the cationic monomer to the anionic monomer is about 1:1 so that the salt form of the monomer pair is present.

The copolymers, described herein, are synthesized from salts derived predominantly from oppositely charged monomers, and generally spontaneously form alternating polymers. Copolymers of this sort have no formal fixed ion exchange sites, but instead interact with salts by electrostatic interactions with oppositely charged monomer pairs which are adjacent in the copolymer backbone. The extent to which the copolymer is actually formed with alternating monomers is dependent upon the relative reactivity of the monomer pair, the concentration of the monomers during polymerization, and the presence of other electrolytes during polymerization. The ratio r of the monomer reactivity ratios of the two monomers is usually a good indicator of the copolymer type. For example when the r<1 then there is more probability that the $1^{st}$ monomer will react with a $2^{nd}$ monomer to continue chain growth. This is usually the case when the two monomers have similar reactivity. In this case the resulting copolymer is an alternating kind. If on the other hand r>1 there is greater probability that the $1^{st}$ monomer would react with itself than with the $2^{nd}$ monomer. Usually this results in the formation of a block copolymer. More details regarding reactivity ratios can be obtained from the Polymer Handbook, J. Brandrup and E.H. Immergut, John Wiley and Sons $3^{rd}$ edition, 1989, p 153 to 266, which is hereby fully incorporated by reference herein. Dimethylaminoethylacrylate and acrylic acid have about the same reactivity ratio values so that the copolymer forms a predominantly alternating copolymer. Copolymers synthesized from these two monomers in 1:1 mole ratio tend to sorb deionized water and concentrated electrolyte solutions to a similar extent.

However, by choosing monomers which have significantly different reactivity ratios (i.e., the ratio r of the reactivity ratios of the two monomers is >1), especially when reacted at high concentration, the resulting copolymer will contain regions with excess concentrations of one of the monomers. As an example, the high concentration can describe a situation where the first monomer is 1.1× to 100× the concentration of the second monomer. In this case, significant amounts of electrostatic cross-linking will exist in deionized water.

An example of such a system is the combination of acrylate with dimethylaminoethylmethacrylate. This system, although a bit more expensive because of the higher equivalent weight of dimethylaminoethylmethacrylate, forms copolymers which sorb considerably more water containing electrolyte than deionized water. The extent of electrostatic crosslinking in the case of this copolymer system is such that even uncrosslinked copolymer will not dissolve in deionized water even though the same uncross-linked dissolves readily in 10% NaCl.

Copolymers which preferentially sorb low ionic strength solutions can be synthesized with higher mole ratios of acrylic acid relative to dimethylaminoethylacrylate. For example, the molar ratio could vary from 1:5 to 1:100. Similarly copolymer which preferentially sorbs high ionic strength solutions is best constructed from monomers with significantly different reactivity ratios (e.g., r>1). Examples of such systems include dimethylaminoethylmethacrylate and acrylate as well as dimethylaminoethylacrylate and methacrylate.

Cross-linkers suitable for use with a first and second copolymer can include a wide variety of water soluble diacrylates and dimethacrylates. In addition, the crosslinker can include a polyethylene glycol spacer. Acrylate or methacrylate based cross-linkers are widely available, generally nontoxic and inexpensive and thus suitable for use in the copolymers described herein. In an embodiment, the cross-linker may range from about 0.1% to about 3% by weight of the polymeric drying agent.

Initiators suitable for use in the polymeric drying agent include any water soluble initiator commonly employed in free radical polymerization. This includes redox initiator systems such as the persulfate/metabisulfite initiator system as well as azo amidine initiators such as V50 from Wako Chemical or azobiscyanovaleric acid.

EXAMPLE 1

Synthesis of the first copolymer was based on a weak acid monomer and a weak base monomer. 4.0 g of acrylic acid, (Sigma Aldrich) monomer was added to 25 g of water followed by 0.016 g of polyethylene glycol 600 diacrylate (Sartomer) as a crosslinker and mixed in an amber glass bottle. Next, 7.95 g of dimethylaminoethylacrylate (Sigma Aldrich) monomer was added to this mixture and mixed until a homogeneous solution was obtained. At this point, the acrylic acid is in the carboxylate form and tertiary amine group is protonated. The molar ratio of acrylic acid to dimethylaminoethylacrylate was 1:1. 0.091 g of the initiator V50 [2,2'-azobis (2-amidinopropane) dihydrochloride] (Wako Chemicals) was dissolved in 2 g of water and added to the monomer mixture and mixed further until the mixture was homogeneous. The reaction mixture was then allowed to polymerize in a closed container at 50° C. for 2 hrs. The product was a soft gel at this point. The polymer mass was separated from the container and then shredded into several pieces and then allowed to dry at 65-70° C. for 24-48 hrs. The resulting product was a hard and glassy solid and was further ground to a fine powder form of the copolymer.

EXAMPLE 2

The water sorption capacity of the first copolymer from Example 1 was tested under a range of salt concentrations as listed below in Table 1. The first column of Table 1 describes the type of aqueous salt solution. The second column of Table 1 lists the grams of solution sorbed by one gram of the first copolymer. This test was performed visually where a person observed the amount of water sorbed by the polymer. The capacity of the first copolymer was exceeded when water was visually observed to be unassociated with the first copolymer. It is clear that this copolymer sorbs up to about 50 to 70 times its weight under a wide range ionic strength conditions up to about 10% salt. Thus, the first copolymer is well-suited for sorbing water from samples containing an unknown amount of salt.

TABLE 1

Sorption test of the copolymer

| Solvent tested | Sorption ratio (water:1$^{st}$ copolymer) |
|---|---|
| Deionized water | +70:1 |
| Tapwater | +60:1 |
| 1% NaCl | +60:1 |
| 2.5% NaCl | +60:1 |
| 10% NaCl | +70:1 |
| 1% calcium chloride | +50:1 |
| 2.5% calcium chloride | +50:1 |
| 10% calcium chloride | +60:1 |
| 1% aluminum chloride | +50:1 |
| 2.5% aluminum chloride | +50:1 |
| 10% aluminum chloride | +50:1 |

EXAMPLE 3

Synthesis of the second copolymer based on a strong acid monomer and a strong base monomer. The monomer [3-(methacryloylamino) propyl] trimethylammonium chloride (50% w/w aqueous solution, Sigma Aldrich) was purified by passing through a bed containing activated carbon. [3-(methacryloylamino) propyl] trimethylammonium chloride (50% w/w aqueous solution, Sigma Aldrich) contains some (about 600 ppm) monomethyl ether of hydroquinone (MEHQ) as an inhibitor. MEHQ was removed so that it could not potentially leach out of the copolymer affecting the analysis in extraction applications.

9.4 g of 2-acrylamido-2-methyl-1-propanesulfonic acid monomer was added into a plastic container containing 9.4 g of deionized water. The mass was stirred and mixed thoroughly to dissolve the solid monomer. The strong acid was neutralized with the addition of equimolar NaOH (3.62 g of 50% NaOH) in the container with constant stirring to mix and cool the solution (at room temperature). 0.193 g of the crosslinker N,N'-methylenebis(acrylamide) (Sigma Aldrich) was added to the above mixture and mixed. 20.03 g of [3-(methacryloylamino) propyl] trimethylammonium chloride monomer (50% w/w aqueous solution) was added to the resulting mixture and mixed thoroughly until the mixture was homogeneous. The molar ratio of 2-acrylamido-2-methyl-1-propanesulfonic acid to [3-(methacryloylamino) propyl]trimethylammonium chloride was 1:1. 0.193 g of the initiator V50 [2,2'-azobis (2-amidinopropane) dihydrochloride] (Wako Chemicals) was dissolved in 2 g of water and then added to the above mixture and mixed until homogeneous. The reaction mixture was then allowed to polymerize in a closed container at 50° C. for 2 hrs. The product was a brittle gel at this point. The gel copolymer mass was taken out of the container and then broken into small pieces using a blender and then allowed to dry at 65-70° C. for 24-48 hrs. The product was a brittle cluster of small particles after drying. The product was ground further in a blender resulting in a homogenous copolymer mixture.

EXAMPLE 4

The water removal capacity of the first copolymer from Example 1 was tested under solvent extraction conditions at room temperature. A known amount of water (1 g) and hexane (5-10 mL) were added into a 40 mL glass bottle to evaluate the water removal capability of the water sorbent copolymer in the presence of hexane. The organic phase hexane and the water phase separate clearly and can be visually examined for the disappearance of the water phase in the presence of the first copolymer. The amount of water sorbent copolymer needed was 0.0862 g to sorb 1.001 g of water for test-1. Similarly, the amount of water sorbent copolymer needed was 0.0922 g to sorb 0.9963 g of water for test-2. The data was reported in Table 2. The calculated grams of $H_2O$ removed were 11.65 g and 10.81 g per g of water sorbent copolymer for test-1 and test-2, respectively. These water removal capacities were much better than the water removal capacity of a sodium sulfate salt as shown in Table 2. The first copolymer became a soft gel after sorbing the water.

TABLE 2

Water removal capacity of water sorbent 1$^{st}$ copolymer and Na2SO4.

| | Grams of 1$^{st}$ copolymer needed to sorb per g water | Grams of $Na_2SO_4$ needed to sorb per g water | Grams of $H_2O$ removed per g of 1$^{st}$ copolymer | Grams of $H_2O$ removed per g of $Na_2SO_4$ (control) |
|---|---|---|---|---|
| Test-1 | 0.0861 | 3.436 | 11.65 | 0.291 |
| Test-2 | 0.0925 | 4.016 | 10.81 | 0.249 |

EXAMPLE 5

The water removal capacity of the second copolymer from Example 3 was measured following the same steps as outlined in Example 4. The amount of water sorbent copolymer needed was 0.160 g and 0.202 g respectively for two different batches of the copolymer for sorbing one gram of water, as shown in Table 3. The second copolymer maintained a particle form even after sorbing the water making it easier to handle relative to the first copolymer of Example 1 which was a gel like form. Thus, the second copolymer can be easily removed by filtering or decanting.

TABLE 3

Water removal capacity of water sorbent 2$^{nd}$ copolymer and $Na_2SO_4$.

| | Grams of 2$^{nd}$ copolymer needed to sorb per g water | Grams of $H_2O$ removed per g of 2$^{nd}$ copolymer |
|---|---|---|
| Batch-A | 0.160 | 6.25 |
| Batch-B | 0.202 | 4.95 |

EXAMPLE 6

The in-cell configuration was tested using a commercial extraction instrument ASE 350 (Thermo Fisher Scientific) that performed solid liquid extractions at high temperature and pressure. A simulated sample was prepared by spiking 10 g of water onto 5 g of diatomaceous earth (DE) and loaded into a 34 mL sample container. The extraction was performed at 100° C. using the conditions listed below. A water breakthrough of 3.13 g was observed in the collection bottle. It should be noted that a polymeric drying agent was not added to the sample container for this experiment.
ASE 350 extraction conditions:
Temperature: 100° C.
Static time: 5 min
Cycles: 1
Flush: 10%
Purge: 60 sec
Solvent: Hexane

EXAMPLE 7

The first copolymer from Example 1 was used for in-cell water removal. The experimental setup was similar to Example 6 except that the first copolymer was added to the sample container. 5 g of DE and 1 g of the first copolymer from Example 1 was added to the sample container and the extraction proceeded using the same conditions listed in Example 6. Unlike Example 6, there was no breakthrough of water, as shown in Table 4. Thus, the first copolymer is capable of in-cell water removal even at 100° C.

TABLE 4

In-cell water removal capacity of the copolymer at 100° C. in ASE

| Temp., ° C. | Total water present in the cell, g | Dispersant | Water observed in the collection bottle, g |
|---|---|---|---|
| 100 | 10 | 5 g DE | 3.13 |
| 100 | 10.04 | 5 g DE and 1 g of first copolymer | No |

EXAMPLE 8

The second copolymer from Example 3 was tested for in-cell water removal in an ASE 350 system at various extraction temperatures. The results are shown below in Table 5. Unlike the first copolymer from the weak acid weak base combination from Example 1 that became a soft gel after the extraction, the strong acid strong base combination of Example 3 provided a copolymer that retained its conformation and could be used by itself or in conjunction with DE. It should be noted that the water removal efficiency dropped as the temperature increased, nevertheless practical water removal was still feasible even at 150° C.
ASE 350 extraction condition:
Temperature: 100° C.-175° C.
Static time: 10 min
Cycles: 3
Flush: 75%
Purge: 120 sec
Solvent: Hexane

TABLE 5

In-cell water removal capacity of the copolymer (from Example 3) at different temperatures in ASE

| Temp., ° C. | Total water present in the cell, g | 2$^{nd}$ Copolymer/ Dispersant | Water observed in the collection bottle, g |
|---|---|---|---|
| 100 | 4.0 | 4 g of 2$^{nd}$ copolymer | No |
| 110 | 3.5 | 4 g of 2$^{nd}$ copolymer | No |
| 125 | 2.2 | 4 g of 2$^{nd}$ copolymer | No |
| 150 | 1.5 | 4 g of 2$^{nd}$ copolymer | No |

EXAMPLE 9

The effect of increasing the amount of cross-linker was studied using the second copolymer from Example 3. Four different embodiments of the second copolymer were synthesized by using the following four amounts of the cross-linker (N,N-methylenebisacrylamide) that are 0.5%, 1.0%, 2.0% and 3.0%. The copolymers were tested for moisture removal as previously done with hexane and 1 g of added water.

At room temperature, the moisture removal data indicated higher amounts of the second copolymer were needed to remove 1 g of water as the crosslinking increased. For example, in order to absorb 1 g of water by a copolymer having crosslinking % of 0.5%, 1%, 2% and 3% respectively, the amount of the copolymer needed increased from 0.14 g, 0.17 g, 0.25 g and 0.27 g respectively. The results indicate that higher levels of crosslinking restricted the swelling, and thus, decreased the sorbing of moisture.

The copolymers from this Example were also tested for moisture removal at 150° C., as shown in Table 6. The amount of copolymer was adjusted based on the water removal efficiency measured from above. The bulk of the added water was removed in all cases with a small amount of breakthrough showing the utility of the copolymer formulations for moisture removal at higher temperatures.

ASE 350 extraction condition:
Temperature: 150° C.
Static time: 10 min
Cycles: 3
Flush: 75%
Purge: 120 sec
Solvent: Hexane

TABLE 6

Effect of crosslinking on water removal capacity of the second copolymer having four different levels of crosslinker, in-cell at 150° C.

| Amount of cross-linking, % | Water in the cell, g | Amount of $2^{nd}$ copolymer in the cell, g | Water observed in the collection bottle, g |
|---|---|---|---|
| 0.5 | 2.2 | 3.4 | 0.11 |
| 1.0 | 2.2 | 4.0 | 0.08 |
| 2 | 2.2 | 5.9 | 0.13 |
| 3 | 2.2 | 6.4 | 0.16 |

EXAMPLE 10

Analyte recovery from ASE extraction using the second copolymer from Example 3 was studied using a mixture of phenols. An in-cell extraction was performed by adding 8 g of the second copolymer, a 1.5 mL aliquot of the phenol mixture in acetonitrile, and 8.5 mL of water to a sample container. Note that each phenol species had a concentration of 30 µg/mL in the 10 mL extract. The phenol mixture sample was then extracted in an ASE 350 instrument using a 1:1 ratio of dichloromethane:acetone solvent at an extraction temperature of 100° C. The extraction conditions are outlined below. The extract was evaporated to 10 mL under nitrogen stream at 40° C.

ASE 350 extraction condition:
Temperature: 100° C.
Static time: 5 min
Cycles: 3
Flush: 60%
Purge: 120 sec
Solvent: 1/1 acetone/Dichloromethane The 10 mL extract was analyzed using high performance liquid chromatography (HPLC) instrument (Thermo Fisher Scientific). The HPLC set up had a P680 pump, AS50 auto sampler, PDA-100 photodiode array detector and a chromatographic oven. Chromeleon 6.8 operating system was used for data acquisition and control. The separation column used was Acclaim Polar Advantage C16 5 µm 4.6×150 mm. The flow rate was 1.0 mL/min. The separation was based on gradient elution of A, 25 mM HAc/NH$_4$Ac and B, acetonitrile where composition of B changes from 25% to 70% in a period of 0 to 17.5 min. The detection wavelength used was 280 nm.

The results from this Example are shown in Table 7. The % recovery data showed acceptable performance based on an acceptance criteria of being within 30%.

TABLE 7

Recovery of analytes for an in-cell extraction of phenol mixture in water using the second copolymer as a drying agent at 100° C.

| | Analytes | Total spike level in 10 mL µg | Analysis result µg/mL | Relative Standard Deviation % | Total amount in final extract µg | % recovery |
|---|---|---|---|---|---|---|
| 1 | 2,4-Dinitrophenol | 300 | 24.30 | 0.80 | 243.03 | 81.01 |
| 2 | Phenol | 300 | 27.00 | 0.40 | 269.97 | 89.99 |
| 3 | P-Toluidine | 300 | 26.02 | 5.95 | 260.17 | 86.72 |
| 4 | 4-Nitrophenol | 300 | 28.82 | 0.52 | 288.16 | 96.05 |
| 5 | 2-Chlorophenol | 300 | 27.70 | 0.07 | 277.00 | 92.33 |
| 6 | 4-ethylaniline | 300 | 27.85 | 1.66 | 278.47 | 92.82 |
| 7 | 4-Chloroaniline | 300 | 28.33 | 1.82 | 281.48 | 94.44 |
| 8 | 2-Nitrophenol | 300 | 28.15 | 0.76 | 283.31 | 93.83 |
| 9 | 2,4-Dichlorophenol | 300 | 29.25 | 1.07 | 292.50 | 97.50 |
| 10 | 2,4,6-Trichlorophenol | 300 | 29.25 | 0.26 | 292.52 | 97.51 |

EXAMPLE 11

In this example the moisture removal capacity of the second copolymer from Example 3 was tested in-cell with or without added DE. The purpose of the DE was to improve the flow characteristics of the solvent to maximize exposure to the second copolymer. ASE extraction conditions are listed below. The ASE extraction was performed at 100° C. The results on Table 8 indicated that the copolymer and DE combination produced excellent results in regards to sorbing water at elevated temperature. The improved results are attributed to homogenous flow in the vicinity of the copolymer. The net effect is improved usage of the second copolymer.

ASE 350 extraction condition:
Temperature: 100° C.
Static time: 5 min
Cycles: 3
Flush: 30%
Purge: 120 sec
Solvent: Hexane

TABLE 8

ASE in-cell water removal capacity of only second copolymer, only DE, and the combination of second copolymer and DE at 100° C.

| Temp., ° C. | Total water present in the cell, g | Dispersant | Water observed in the collection bottle, g |
|---|---|---|---|
| 100 | 8.26 | 8 g $2^{nd}$ copolymer | 0.13 |
| 100 | 8.00 | 8 g DE | 0.07 |
| 100 | 8.22 | 4 g 2nd copolymer and 4 g DE | No |

EXAMPLE 12

This Example is similar to Example 11 except that the ASE extraction is performed at a higher temperature of 150° C. The results in Table 9 indicated that the second copolymer and DE combination produced excellent results in regards to sorbing water at the elevated temperature 150° C. The improved results are attributed to homogenous flow in the vicinity of the copolymer. The net effect is improved usage of the copolymer.

ASE 350 conditions
Temperature: 150° C.
Static time: 10 min
Cycles: 3
Flush: 75%
Purge: 120 sec
Solvent: Hexane

TABLE 9

ASE in-cell water removal capacity of only copolymer, only DE, and the combination of second copolymer and DE at 150° C.

| Temp., ° C. | Total water present in the cell, g | Dispersant | Water observed in the collection bottle, g |
|---|---|---|---|
| 150 | 2.15 | 4 g $2^{nd}$ copolymer | 0.10 |
| 150 | 2.03 | 4 g DE | 0.20 |
| 150 | 2.15 | 2 g 2nd copolymer, 2 g DE | No |

EXAMPLE 13

This Example will demonstrate that the second polymer sorbs water more effectively than the prior art polymer described as crosslinked-polyacrylate material (Waste lock 770 polymer, $M^2$ Polymer Technologies, Inc.). Additionally, this example will show that the second polymer can effectively sorb water over a much wider range of salt concentrations than the prior art polymer. In this Example, a type of polymer (i.e. $2^{nd}$ copolymer or Waste lock 770 polymer) was added to an aqueous solution to determine the amount required to sorb one gram of water. The water solution contained a salt concentration ranging from 0 to about 26.5% NaCl. The results in Table 10 show that the water removal capacity of the second polymer was substantially unaffected by the salt concentration. Approximately the same amount of the second polymer was required for sorbing one gram of aqueous solutions containing 0 to 26.5% NaCl. In contrast, the polyacrylate based polymer sorbed substantially less water when the salt concentration was increased. In addition, the second copolymer sorbed substantially more water per gram of polymer than the polyacrylate based polymer for solutions containing zero to 2.91% NaCl.

TABLE 10

Water removal capacity of water absorbent 2nd polymer versus a commercial polyacrylate based polymer at room temperature.

| | Grams of polymer needed to sorb per g of water | Grams of polymer needed to sorb per g of 2.91% NaCl solution (sea water concentration) | Grams of polymer needed to sorb per g of 26.5% NaCl solution (saturation level concentration) |
|---|---|---|---|
| 2nd copolymer | 0.20 | 0.19 | 0.18 |
| Polyacrylate based polymer | 0.04 | 0.08 | 0.27 |

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:
1. A method of drying a sample, where the sample includes water, the method comprising:
adding the sample and a polymeric drying agent to a container, the polymeric drying agent comprising a copolymer of at least a cationic monomer, an anionic monomer, and a crosslinker, in which the sample includes water and an analyte, the cationic monomer comprises [3-methylacryloylamino)propyl]trimethylammonium chloride, the anionic monomer comprises 2-acrylamido-2-methyl-1-propanesulfonic acid, and the crosslinker comprises N,N'-methylenebis(acrylamide); and sorbing the water from the sample to the polymeric drying agent.

2. The method of claim 1 further comprising:
removing the analyte from the container.

3. The method of claim 2 further comprising:
analyzing the analyte using an analytical technique, in which the analytical technique is one of a liquid chromatography, a mass spectrometry, a gas chromatography, an ultraviolet-visible spectroscopy, a fluorescence spectroscopy, a flame ionization detection, an electrochemical detection, and a combination thereof.

4. The method of claim 2, in which the removing of the analyte includes one of a filtering process or a decanting process.

5. The method of claim 1, in which substantially all of the water is sorbed from the sample by the polymeric drying agent.

6. The method of claim 5, in which the container has less than about 100 microliters of water after the polymeric drying agent has sorbed the water.

7. The method of claim 1, in which before the adding of the sample and the polymeric drying agent to the container, the analyte from the sample is dissolved into a solvent.

8. The method of claim 1, in which a molar ratio of the cationic monomer to the anionic monomer is about 1:1.

9. The method of claim 1, in which the crosslinker ranges from about 0.1% to about 3% by weight of the polymeric drying agent.

10. The method of claim 1 further comprises: heating the container to an elevated temperature greater than ambient, in which the elevated temperature ranges from about 40° C. to about 100° C.

11. The method of claim 1, in which the polymeric drying agent sorbs up to about 1 gram of water per gram of the polymeric drying agent.

12. The method of claim 10, in which the polymeric drying agent sorbs up to about 0.38 grams of water per gram of the polymeric drying agent.

13. The method of claim 10, in which an increased pressure in the container ranges from about 100 pounds per square inch to about 1500 pounds per square inch.

14. The method of claim 1 further comprising: adding a diatomaceous earth material to the container with the sample and the polymeric drying agent.

15. The method of claim 1 further comprising: mixing the sample and the polymeric drying agent together.

* * * * *